(12) United States Patent
Heslet

(10) Patent No.: US 11,813,309 B2
(45) Date of Patent: Nov. 14, 2023

(54) METHOD OF ALLEVIATING CHRONIC WOUNDS

(71) Applicant: Reponex Pharmaceuticals APS, Hørsholm (DK)

(72) Inventor: Lars Heslet, Gentofte (DK)

(73) Assignee: Reponex Pharmaceuticals APS, Hørsholm (DK)

( * ) Notice: Subject to any disclaimer, the term of this patent is extended or adjusted under 35 U.S.C. 154(b) by 0 days.

(21) Appl. No.: 16/366,898

(22) Filed: Mar. 27, 2019

(65) Prior Publication Data
US 2020/0030410 A1 Jan. 30, 2020

Related U.S. Application Data

(63) Continuation of application No. 15/313,384, filed as application No. PCT/EP2015/061598 on May 26, 2015, now abandoned.

(30) Foreign Application Priority Data

May 23, 2014 (DK) .......................... PA 2014 70300

(51) Int. Cl.
| | | |
|---|---|---|
| *A61K 38/17* | (2006.01) | |
| *A61K 38/19* | (2006.01) | |
| *A61K 31/7024* | (2006.01) | |
| *A61K 31/728* | (2006.01) | |
| *A61K 47/26* | (2006.01) | |
| *A61K 47/36* | (2006.01) | |
| *A61K 9/10* | (2006.01) | |
| *A61K 47/24* | (2006.01) | |
| *A61K 9/00* | (2006.01) | |

(52) U.S. Cl.
CPC ........ *A61K 38/193* (2013.01); *A61K 31/7024* (2013.01); *A61K 31/728* (2013.01); *A61K 47/26* (2013.01); *A61K 9/0014* (2013.01); *A61K 9/10* (2013.01); *A61K 47/24* (2013.01); *A61K 47/36* (2013.01)

(58) Field of Classification Search
CPC ............................ A61K 38/193; A61K 31/728
See application file for complete search history.

(56) References Cited

U.S. PATENT DOCUMENTS

| | | | | |
|---|---|---|---|---|
| 5,166,331 | A | * 11/1992 | della Valle | ........... A61K 9/0014 536/55.1 |
| 2004/0077540 | A1 | 4/2004 | Quay | |
| 2009/0227537 | A1 | 9/2009 | Grady | |
| 2010/0015217 | A1* | 1/2010 | Fiala | ....................... A61P 31/04 424/450 |
| 2012/0202767 | A1* | 8/2012 | Di Schiena | .......... A61K 9/0095 514/53 |

FOREIGN PATENT DOCUMENTS

| | | |
|---|---|---|
| CA | 2020200 | 12/1991 |
| JP | 09-05-506673 | 9/1992 |
| WO | WO 92/14480 A1 | 9/1992 |
| WO | WO 93/07891 * | 7/1993 |
| WO | WO 2008/116116 A2 | 9/2008 |
| WO | WO 2013/007960 A1 | 1/2013 |
| WO | WO 2014/128173 A1 | 8/2014 |

OTHER PUBLICATIONS

Fang et al., 458-467, (2007), impaired cutaneous wound healing in GM-CSF knockout mice, British J. Dermatology, 157, 458-467, (2007).*
Mann et al., Granulocyte-macrophage colony stimulating factor, Journal of Investigative Dermatology Symposium Proceedings, vol. 11, 87-92, (2006).*
Lim et al. PLOSone( 2013), Regulation of wound healing by GM-CSF after vocal fold injury.*
Xu et al., Soft. Matter, 8: 3280-3294, (2012).*
Liao et al. , Drug Delivery 12: 327-342, (2005).*
International Search Report for PCT/EP2015/061598 dated Dec. 18, 2015.
Notice of Reasons of Rejection (with translation) dated Jan. 22, 2019 in JP-2016-569410.

* cited by examiner

*Primary Examiner* — Gyan Chandra
(74) *Attorney, Agent, or Firm* — Knobbe, Martens, Olson & Bear, LLP

(57) ABSTRACT

The present invention provides compositions comprising granulocyte-macrophage colony-stimulating factor (GM-CSF), sucrose octasulfate or sucralfate and hyaluronic acid for the treatment, pre-emptive treatment or prophylaxis of ulcers, wounds and other injuries to the skin or membranes of the body. Other aspects of the invention are methods of treatment or prevention using the compositions described, as well as an application device for use in the methods provided.

21 Claims, 1 Drawing Sheet
Specification includes a Sequence Listing.

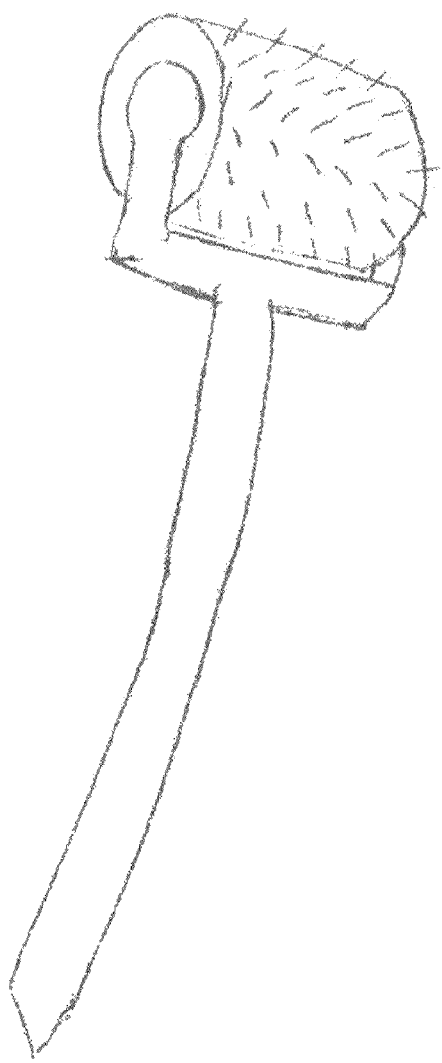

METHOD OF ALLEVIATING CHRONIC WOUNDS

CROSS REFERENCE TO RELATED APPLICATIONS

This application is a continuation of U.S. patent application Ser. No. 15/313,384, filed Nov. 22, 2016, which is a U.S. National Phase Application of PCT International Application Number PCT/EP2015/061598, filed on May 26, 2015, designating the United States of America and published in the English language, which is an International Application of and claims the benefit of priority to Danish Patent Application No. PA 2014 70300, filed on May 23, 2014. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 2019-03-26Sequence_Listing_ZACCO108.005C1.TXT. The ASCII text file was created on Jun. 5, 2015, and updated on Mar. 26, 2019. The size of the ASCII text file is 3 KB.

FIELD OF THE INVENTION

The present invention provides compositions comprising granulocyte-macrophage colony-stimulating factor (GM-CSF), sucrose octasulfate (SOS) or its basic aluminum salt, sucralfate, and hyaluronic acid for the treatment, pre-emptive therapy or prophylaxis of ulcers, wounds and other injuries to the skin or mucous membranes of the body. Other aspects of the invention are methods of treatment or prevention using the compositions described herein, as well as an application-device for use in the methods provided herein.

BACKGROUND OF THE INVENTION

Wound healing, which is a normal biological process in the human body, is achieved through dynamic, interactive processes involving cells and extracellular matrix, and depends on both internal and external factors. The healing process has historically been described as consisting of four precisely and highly programmed phases: hemostasis, inflammation, proliferation, and remodeling. For a wound to heal optimally, all four phases must occur in the proper sequence and time frame. Many factors influence this process and may cause abnormal or impaired wound healing, resulting in so-called "non-healing wounds". These wounds have generally failed to progress through the normal stages of healing. Such wounds often enter a state of pathologic inflammation due to a postponed, incomplete, or uncoordinated healing process. Most chronic wounds are ulcers that are associated with venous stasis, diabetes mellitus, ischemic, or pressure. Non-healing wounds affect more than 1% of the population of the industrialized World. In the United States alone, non-healing wounds affect up to 6 million people, with persons aged 65 years or more accounting for 85% of these cases. Non-healing wounds result in an enormous health care expenditure, the total cost being estimated at more than $3 billion per year.

The incidence is expected to increase as the population ages and as the number of individuals with diabetes increases. Chronic ulcers negatively affect the patients' quality of life and productivity, and will impose an increasing financial burden on the health care system.

Ulcers of the lower extremities, especially those attributed to diabetes, venous disease, or arterial disease, comprise a substantial proportion of chronic ulcers. Approximately 15-25% of individuals with diabetes develop a foot ulcer at some point in their lifetime and an estimated 12% of these patients require lower extremity amputation. Healing is complicated by diabetic neuropathy and susceptibility to infection is increased by a factor of four in diabetic foot ulcer patients. Venous disease accounts for the majority of chronic lower extremity ulcers. Venous hypertension of varying etiology can damage vessel walls and ultimately lead to skin breakdown. Arterial ulcers are less common and result from of impaired circulation which impairs healing.

Standard treatment for all non-healing wounds and ulcers includes debridement of necrotic tissue, control of infection and local wound care. For each category of non-healing wounds, specialized treatment modalities have to be employed. For diabetic foot ulcers there also has to be focus on mechanical off-loading, management of blood glucose levels, and education on foot care. Treatment of venous ulcers has typically included the use of mechanical compression and limb elevation to reverse tissue edema and improve venous blood flow. Care for ulcers caused by arterial insufficiency is centered on reestablishing blood flow and minimizing further loss of tissue perfusion. For pressure ulcers, off-loading methods or devices are the gold standard of treatment.

If ulcers do not adequately heal with standard treatment, additional treatment modalities may be required; these are often termed "advanced wound care therapies". While ulcers of the lower extremities are frequently classified etiologically as diabetic, venous, arterial or pressure-related, overlap may exist. Treatment modalities and wound care therapies are often selected on the basis of ulcer characteristics as well as patient factors, past treatment, and provider preference. A large and growing array of advanced wound care therapies of different components and indications has been developed. For a considerable number of these therapies, the efficacy, comparative effectiveness and adverse effects are not well established and the evidence for effectiveness is weak. Thus, although there has been extensive research in the field of wound treatment, promoting the healing of wounds and ulcers is still a complex task, particularly in elderly or diseased patients.

U.S. Pat. No. 6,689,351 discloses the topical application of GM-CSF for the treatment of wounds. The application does not disclose a composition comprising GM-CSF, sucrose octasulfate and hyaluronic acid for subcutaneous or intracutaneous application for treating wounds.

Makkonen et al. (2000) have disclosed the combination of GM-CSF and sucralfate. GM-CSF was administered subcutaneously and sucralfate was administered as a mouthwash. The article does not disclose a composition comprising hyaluronic acid.

Saarilahti et al. (2002) have disclosed the use of GM-CSF or sucralfate for the treatment of radiation-induced mucositis. The article does not disclose a composition comprising GM-CSF, sucralfate and hyaluronic acid.

SUMMARY OF THE INVENTION

The present invention provides a composition comprising granulocyte-macrophage-colony stimulating factor (GM- CSF) or a fragment or variant thereof, sucrose octasulfate (SOS) or sucralfate, and hyaluronic acid. Such a composition is useful for the prophylaxis, preemptive therapy and the treatment of ulcers, wounds and other injuries to the skin or mucous membranes or connective tissues of the body, as well as the treatment of abnormal scarring (hyperkeratotic scarring and keloid formation). The authors have found that the compositions of the present invention are particularly useful compared to other types of wound treatment previously described.

It is an aspect of the invention to provide a roller tool for applying the composition according to the invention to the wound area. Such a roller tool may comprise protrusions allowing the compositions as described herein to penetrate into the intracutaneous or subcutaneous layers of the skin.

It is further an aspect of the invention to provide a method for treatment, prevention or alleviation of irritation or lesion such as wounds, chronic skin lesions, scars and other lesions of the skin, mucosal membranes or connective tissue of the body of a subject, the method comprising administering to the subject an effective amount of a composition according to the present invention.

DESCRIPTION OF THE FIGURE

FIG. 1: Roller tool for administering the composition of the present invention. The use of a spiked roller is called "hedge-hogging". The roller tool comprises a cylindrical roller body having a length and an interior, with two opposingly disposed circular end surfaces and an endless surface. The circular end surfaces each have an aperture in their center, and the endless surface incorporates randomly spaced spikes or protrusions. The roller body is held by a U-shaped frame terminating in two end flanges rotatably engaging the circular end surfaces of the roller body. The flanges each define a flange aperture proximate to the apertures in the circular end surfaces of the roller body, so that the end flanges can be removably secured to the circular end surfaces of the roller body. A handle is attached to the center of the U-shaped frame to facilitate the manipulation of the roller body.

DETAILED DESCRIPTION OF THE INVENTION

The present invention provides a composition comprising granulocyte-macrophage-colony stimulating factor (GM-CSF) or a fragment or variant thereof, sucrose octasulfate (SOS) or a derivative or salt thereof, such as sucralfate, and hyaluronic acid (HA). Such a composition is useful for the treatment, preemptive therapy and prophylaxis of ulcers, wounds and other injuries to the skin or mucous membranes or connective tissues of the body and may be applied by different techniques. Thus, the present invention further provides methods for the use of the compositions of the present invention as well as an application device for the treatment of wounds, chronic skin lesions and/or other injuries to the skin or mucous membranes.

The normal process of healing of a lesion in the skin or a mucous membrane typically proceeds via four distinct sequential stages or phases, namely hemostasis, inflammation, proliferation and remodeling or maturation.

Hemostasis is the vascular response stage that occurs immediately after the insult and normally lasts for up to a few hours in humans. The wound may bleed initially, but blood clotting together with vasoconstriction re-establishes hemostasis and provides a provisional extracellular matrix for cell migration.

Inflammation normally starts at injury and finishes within 3-4 days in normal healing. The inflammation phase is recognized clinically by the classical features of heat, redness, edema and pain. The wound starts to exude fluid which serves to remove debris, and proteases are released into the wound area. White blood cells and macrophages begin to congregate in the lesion zone, the former to clear debris and the latter for phagocytosis and to release growth factors to stimulate fibroblasts. During this phase, the extracellular matrix is constructed.

The proliferation phase normally continues the inflammatory phase and is characterized by fibroblast proliferation and migration, and the production of connective tissue. It starts about day 4 after the tissue trauma and continues for 2-3 weeks after the trauma in case of a closed wound. This phase can be extended significantly in cases of open wounds with severe tissue damage, when complete closure will require the production of a large amount of connective tissue. During the proliferation phase, the formation of granulation tissue, neovascularization, epithelialization, wound contraction and the laying down of collagen occur.

The maturation phase, sometimes referred to as the remodeling, moderation or scar-forming phase, starts 2-3 weeks after the injury in closed wounds, while it does not start in open wounds before the wound has healed. The maturation phase typically continues for several weeks, months or even years thereafter. Maturation involves contraction of the wound, growth of new epithelial tissue covering the granulation tissue, and possibly scar formation. During this phase myofibroblasts develop from the fibroblasts and the collagen fibers gradually mature and become relatively more organized.

For a wound to heal optimally, all four phases must occur in the proper sequence and time frame. Many factors can influence one or more phases of this process, and may cause abnormal or impaired wound healing, such wounds being called "non-healing" wounds, by causing failure of progress through the normal stages of healing.

Different parts of a wound may heal at different rates, causing some parts of a normal wound to be at a more advanced stage of healing than others.

COMPOSITIONS OF THE INVENTION

Compositions according to the present invention comprise granulocyte-macrophage colony-stimulating factor (GM-CSF) or a fragment or variant thereof, sucrose octasulfate (SOS) or its aluminum salt sucralfate, and hyaluronic acid (HA).

Granulocyte-Macrophage Colony-Stimulating Factor (GM-CSF)

GM-CSF is a member of the family of colony-stimulating factors (CSFs), which are glycoproteins that stimulate the growth of hematopoietic progenitor cells and enhance the functional activity of mature effector cells. In brief, at the early stage of progenitor cell production, CSFs assure the self-renewal of the staminal pool and activate the first stage of hematopoietic differentiation; in the middle stage, when cell proliferation is associated with a progressive acquisition of the characteristics of mature cells, they enormously enhance the number of differentiating cells; in the terminal stage they control the circulation and activation of the mature cells.

GM-CSF has been shown to have a positive effect on wound healing by facilitating wound contraction, causing the local recruitment of inflammatory cells, and inducing keratinocyte proliferation. GM-CSF also activates mononuclear phagocytes, promotes migration of epithelial cells, and further regulates cytokine production in the healing process.

Mature GM-CSF has a monomer protein chain of 127 amino acid residues with several potential glycosylation sites. The variable degree of glycosylation results in a molecular weight range between 14 kDa and 35 kDa. Non-glycosylated and glycosylated GM-CSF show similar activity in vitro (Cebon et al., 1990). The crystallographic analysis of GM-CSF revealed a barrel-shaped structure composed of four short alpha helices (Diederichs et al., 1991). There are two known sequence variants of GM-CSF. The active form of the GM-CSF protein is found extracellularly as a homodimer in vivo.

GM-CSF exerts its biological activity by binding to its receptor. The most important sites of GM-CSF receptor (GM-CSF-R) expression are on the cell surface of myeloid cells, such as macrophages types I & II, epithelial cells and endothelial cells, whereas lymphocytes are GM-CSF-R negative. The native receptor is composed of at least two subunits, alpha and beta. The alpha subunit imparts ligand specificity and binds GM-CSF with nanomolar affinity (Gearing et al., 1989; Gasson et al., 1986). The beta subunit is also part of the interleukin-3 and interleukin-5 receptor complexes and, in association with the GM-CSF receptor alpha subunit and GM-CSF, forms a complex with picomolar binding affinity (Hayashida et al., 1990). The binding domains on GM-CSF for the receptor have been mapped: GM-CSF interacts with the beta subunit of its receptor via a very restricted region in the first alpha helix of GM-CSF (Shanafelt et al., 1991a; Shanafelt et al., 1991 b; Lopez et al., 1991). Binding to the alpha subunit could be mapped to the third alpha helix, helix C, the initial residues of the loop joining helices C and ID, and to the carboxyterminal tail of GM-CSF (Brown et al., 1994).

Formation of the GM-CSF trimeric receptor complex leads to the activation of complex signaling cascades involving molecules of the JAK/STAT families, Shc, Ras, Raf, the MAP kinases, phosphatidylinositol-3-kinase and NFkB, finally leading to transcription of c-myc, c-fos and c-jun. Activation is mainly induced by the beta subunit of the receptor (Hayashida et al., 1990; Kitamura et al., 1991; Sato et al., 1993). The shared beta subunit is also responsible for the overlapping functions exerted by IL-3, IL-5 and GM-CSF (for review see de Groot et al., 1998).

Apart from its hemopoietic growth and differentiation stimulating activity, GM-CSF functions especially as a proinflammatory cytokine. Macrophages, e.g. macrophages of types I & II and monocytes as well as neutrophils and eosinophils are activated by GM-CSF, resulting in the release of other cytokines and chemokines, matrix-degrading proteases, increased HLA expression and increased expression of cell adhesion molecules or receptors for CC-chemokines, which in turn leads to increased chemotaxis of inflammatory cells into inflamed tissue.

When found in wounds, macrophages are known to release a variety of biologically active substances that serve as chemoattractants for both monocytes and fibroblasts, such as transforming growth factor-β (TGF-β) and platelet-derived growth factor (PDGF). Activated macrophages digest devitalized collagen and the fibrin clot. Dissolution of the clot allows the formation of granulation tissue in the wound site, the second wound healing phase.

Exogenous GM-CSF has been shown to restore levels of interleukin 6 (IL-6) and PECAM-1 in a diabetic animal model with delayed wound healing. Exogenous GM-CSF also increases the level of the chemoattractant protein MCP-1 and thereby the recruitment of neutrophils and mononuclear cells in such models, as well as improving re-epithelialization and reducing untoward collagen deposition.

Wong et al. (1985) and Kaushansky et al, (1966) have described the production of recombinant GM-CSF in mammalian cells. Burgess et al. (1987) describes the purification of recombinant GM-CSF produced in *Escherichia coli*.

Functional homologues of GM-CSF: A functional homologue of GM-CSF is a polypeptide having at least 50% sequence identity with the known and naturally occurring sequence of GM-CSF and has one or more GM-CSF functions, such as the stimulation of the growth and differentiation of hematopoietic precursor cells from various lineages, including granulocytes, macrophages, eosinophils and erythrocytes or such as facilitating wound contraction, causing local recruitment of inflammatory cells, such as improving recruitment of neutrophils, inducing keratinocyte proliferation, activating mononuclear phagocytes, promoting migration of epithelial cells, and further regulating cytokine production in the healing process. In one embodiment of the present invention, the variant, functional homologue or analogue of GM-CSF displays biological activity in a human bone marrow assay.

Evolutionary conservation between the GM-CSF protein chains of different closely related species, e.g. assessed by sequence alignment, can be used to pinpoint the degree of evolutionary pressure on individual residues. Preferably, GM-CSF sequences are compared between species where GM-CSF function is conserved, a non-limiting example being mammals, including rodents and primates. Amino-acid residues that are invariant between species are more likely to represent essential amino-acid residues that cannot easily be substituted than residues that change between species. It is evident from the above that a reasonable number of modifications or alterations of the human GM-CSF sequence does not interfere with the activity of the GM-CSF molecule according to the invention. Such GM-CSF molecules are herein referred to as functional equivalents of human GM-CSF, and may be such as variants and fragments of native human GM-CSF as described below.

As used herein, the term "GM-CSF variant" refers to a polypeptide or protein which is homologous to the index protein, which is suitably human GM-CSF, but which differs from the index sequence in that one or more amino-acid residues within the sequence are substituted by other amino-acid residues. Amino-acid substitutions may be regarded as "conservative" when an amino acid is replaced with a different amino acid with broadly similar properties. Non-conservative substitutions refer to the replacement of amino acids amino acids of a different type. Broadly speaking, fewer non-conservative substitutions will be possible without altering the biological activity of the polypeptide or protein. Thus, in one embodiment of the present invention GM-CSF is a variant of the human GM-CSF having the amino acid sequence set forth in SEQ ID NO: 2. In such case, the amino acid sequence set forth in SEQ ID NO: 2 is the index sequence (also referred to as the parent) from which the variants is obtained by one or more amino acid substitutions (or insertions/deletions).

A person skilled in the art will know how to make and assess "conservative" amino-acid substitutions, when one amino acid is substituted by another with one or more shared chemical and/or physical characteristics. Conservative amino-acid substitutions are less likely to affect the functionality of the protein. Amino acids may be grouped according to shared characteristics. A conservative amino-acid substitution is a substitution of one amino acid within a predetermined group of amino acids for another amino acid within the same group, wherein the amino acids within a predetermined groups exhibit similar or substantially similar characteristics. Within the meaning of the term "conservative amino acid substitution" as applied herein, one amino acid may be substituted for another within groups of amino acids characterized by having i) polar side chains (Asp, Glu, Lys, Arg, His, Asn, Gln, Ser, Thr, Tyr, and Cys,)
    ii) non-polar side chains (Gly, Ala, Val, Leu, Ile, Phe, Trp, Pro, and Met)
    iii) aliphatic side chains (Gly, Ala Val, Lou, Ile)
    iv) cyclic side chains (Phe, Tyr, Trp, His, Pro)
    v) aromatic side chains (Phe, Tyr, Trp)
    vi) acidic side chains (Asp, Glu)
    vii) basic side chains (Lys, Arg, His)
    viii) amide side chains (Asn, Gln)
    ix) hydroxy side chains (Ser, Thr)
    x) sulfur-containing side chains (Cys, Met), and/or
    xi) monoamine-dicarboxylic acid structure or mono-amino-monocarboxylic-monoarnidocarboxylic structure (Asp, Glu, Asn. Gln).

A functional homologue or variant of human GM-CSF within the scope of the present invention is a polypeptide that exhibits at least 50% sequence identity with human GM-CSF, such as at least 60% sequence identity, for example at least 70% sequence identity, such as at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with human GM-CSF, while retaining one or more functional properties of GM-CSF as defined above.

Sequence identity can be calculated using a number of well-known algorithms and applying a number of different gap penalties. Any sequence alignment algorithm, such as, but not limited to, FASTA, BLAST, or GETSEQ, may be used for searching homologues and calculating sequence identity. Moreover, when appropriate, any commonly known substitution matrix, such as, but not limited to, PAM, BLOSSUM or PSSM matrices, may be applied with the search algorithm. For example, a PSSM (position-specific scoring matrix) may be applied by means of the PSI-BLAST program. Moreover, sequence alignments may be performed using a range of penalties for gap opening and extension. For example, the BLAST algorithm may be used with a gap-opening penalty in the range of 5-12, and a gap extension penalty in the range 1-2.

Accordingly, a variant or a fragment thereof according to the invention may comprise, within the same variant of the sequence or fragments thereof, or among different variants of the sequence or fragments thereof, one or more substitutions, such as a plurality of substitutions introduced independently of one another.

It is clear from the above outline that the same variant or fragment thereof may comprise more than one conservative amino-acid substitution from more than one group of conservative amino acids as defined herein above.

Aside from the twenty standard amino acids and two special amino acids, selenocysteine and pyrrolysine, there are a vast number of "non-standard amino acids" which are not incorporated into protein in vivo. Examples of nonstandard amino acids include the sulfur-containing taurine and the neurotransmitters GABA and the neurotransmitter precursor DOPA. Other examples are lanthionine, 2-aminoisobutyric acid, and dehydroalanine. Further non-standard amino are ornithine and citrulline.

Non-standard amino acids are usually formed through modifications to standard amino acids. For example, taurine can be formed by the decarboxylation of cysteine, while DOPA is synthesized from tyrosine and hydroxyproline is made by a posttranslational modification of proline (common in collagen), Examples of non-natural amino acids are those listed e.g. in 37 C.F.R. section 1.822(h)(4), all of which are incorporated herein by reference.

Both standard and non-standard amino-acid residues described herein can be in the "D" or "L" isomeric form.

It is contemplated that a functional homologue or variant according to the invention may comprise any amino acid including non-standard amino acids. In preferred embodiments, a functional homologue or variant comprises only standard amino acids.

The standard and/or non-standard amino acids may be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino-acid analogs can be employed instead of the 20 naturally-occurring amino acids. Several such analogs are known, including fluorophenylalanine, norleucine, azetidine-2-carboxylic acid, S-aminoethyl cysteine, 4-methyl tryptophan and the like.

In one embodiment of the present invention, the GM-CSF variant comprises a conjugate capable of prolonging half-life of the active ingredient, such as for example albumin or a fatty acid.

Suitably variants will be at least 60% identical, preferably at least 70% and accordingly, variants preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence of human GM-CSF.

Functional homologues or variants may further comprise chemical modifications such as ubiquitination, labeling (e.g., with radionuclides, various enzymes, etc.), pegylation (derivatization with polyethylene glycol), or by insertion (or substitution by chemical synthesis) of amino acids such as ornithine, which do not normally occur in human proteins.

In addition to the peptidyl compounds described herein, sterically similar compounds may be formulated to mimic the key portions of the peptide structure and that such compounds may also be used in the same manner as the peptides of the invention. This may be achieved by techniques of modelling and chemical design known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications or amidations are also encompassed within the present invention. Functional homologues or variants also comprise glycosylated and covalent or aggregative conjugates formed with the same molecules, including dimers or unrelated chemical moieties. Such functional homologues or variants are prepared by the linkage of functional regions to groups which are found in fragment including at one or both of the N- and C-termini, by means known in the art.

The term "fragment thereof" may refer to any portion of the given amino-acid sequence. Fragments may comprise more than one portion from within the full-length protein, joined together. Suitable fragments may be deletion or addition mutants. The addition of at least one amino acid may be an addition of from preferably 2 to 250 amino acids, such as from 10 to 20 amino acids, for example from 20 to 30 amino acids, such as from 40 to 50 amino acids. Fragments may include small regions from the protein or combinations of these.

Suitable fragments may be deletion or addition mutants. The addition or deletion of at least one amino acid may be an addition or deletion of from preferably 2 to 250 amino acids, such as from 10 to 20 amino acids, for example from 20 to 30 amino acids, such as from 40 to 50 amino acids. The deletion and/or the addition may, independently of one another, be a deletion and/or an addition within a sequence and/or at the end of a sequence.

Deletion mutants suitably comprise at least 20 or 40 consecutive amino acid and more preferably at least 80 or 100 consecutive amino acids in length. Accordingly such a fragment may be a shorter sequence from the sequence of human GM-CSF comprising at least 20 consecutive amino acids, for example at least 30 consecutive amino acids, such as at least 40 consecutive amino acids, for example at least 50 consecutive amino acids, such as at least 60 consecutive amino acids, for example at least 70 consecutive amino acids, such as at least 80 consecutive amino acids, for example at least 90 consecutive amino acids, such as at least 95 consecutive amino acids, such as at least 100 consecutive amino acids, such as at least 105 amino acids, for example at least 110 consecutive amino acids, such as at least 115 consecutive amino acids, for example at least 120 consecutive amino acids, wherein said deletion mutants preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with human GM-CSF.

It is preferred that functional homologues of GM-CSF comprise at the most 500, more preferably at the most 400, even more preferably at the most 300, yet more preferably at the most 200, such as at the most 175, for example at the most 160, such as at the most 150 amino acids, for example at the most 144 amino acids.

There are two known naturally occurring variants of human GM-CSF: a T115I substitution in variant 1 and a I117T substitution in variant 2. Accordingly, in one embodiment of the invention a functional homologue of GM-CSF comprises a sequence with high sequence identity to human GM-CSF (SEQ ID NO:1) or any of the naturally occurring variants.

Analogues of GM-CSF are for example described in U.S. Pat. Nos. 5,229,496, 5,391,485 and 5,393,870. Such analogues are also functional equivalents comprised within the present invention.

In one embodiment, GM-CSF is used according to the present invention in homo- or heteromeric form. Homo- and heteromeric forms of GM-CSF may comprise one or more GM-CSF monomers or functional homologous of GM-CSF as defined herein above. Homo- and heteromers include dimers, trimers, tetramers, pentamers, hexamers, heptamers, octamers, nonamers and decamers.

In one embodiment, a homodimer, trimer or tetramer of GM-CSF is used.

The amino-acid sequence of the precursor (including the signal peptide) form of GM-CSF of Homo sapiens (SEQ ID NO:1) is:
MWLQSLLLLG TVACSISAPA RSPSPSTQPW EHVNAIQEAR RLLNLSRDTA
AEMNETVEVI SEMFDLQEPT CLQTRLELYK QGLRGSLTKL KGPLTMMASH
YKQHCPPTPE TSCATQIITF ESFKENLKDF LLVIPFDCWE PVQE.

The amino-acid sequence of the corresponding mature protein (SEQ ID NO: 2) is:
APARSPSPST QPWEHVNAIQ EARRLLNLSR DTAAEMNETV EVISEMFDLQ
EPTCLQTRLE LYKQGLRGSL TKLKGPLTMM ASHYKQHCPP TPETSCATQI
ITFESFKENL KDFLLVIPFD CWEPVQE GM-CSF according to the present invention may be commercially available, e.g. sargramostim (human recombinant GM-CSF expressed in yeast, such as Leukine®, produced by sanofi-aventis, U.S. LLC., Bridgewater, NJ, USA).

Recombinant Production of GM-CSF

GM-CSF or functional variants or homologues thereof can be produced in various ways, such as isolation from for example human or animal serum or from expression in cells, such as prokaryotic cells, yeast cells, insect cells, mammalian cells or in cell-free systems.

In one embodiment of the invention, GM-CSF is produced recombinantly by host cells. Thus, in one aspect of the present invention, GM-CSF is produced by host cells comprising a first nucleic acid sequence encoding the GM-CSF operably associated with a second nucleic acid capable of directing expression in said host cells. The second nucleic acid sequence may thus comprise or even consist of a promoter that will direct the expression of protein of interest in said cells. A skilled person will be readily capable of identifying useful second nucleic acid sequence for use in a given host cell.

The process of producing a recombinant GM-CSF in general comprises the steps of:
  providing a host cell
  preparing a gene expression construct comprising a first nucleic acid encoding the GM-CSF operably linked to a second nucleic acid capable of directing expression of said protein of interest in the host cell
  transforming the host cell with the construct,
  cultivating the host cell, thereby obtaining expression of the GM-CSF.

The recombinant GM-CSF thus produced may be isolated by any conventional method, such as any of the methods for protein isolation described herein below. The skilled person will be able to identify a suitable protein isolation steps for purifying the GM-CSF.

In one embodiment of the invention, the recombinantly produced GM-CSF is excreted by the host cells. When the GM-CSF is excreted, the process of producing a recombinant protein of interest may comprise the steps of
  providing a host cell
  preparing a gene expression construct comprising a first nucleic acid encoding the GM-CSF operably linked to a second nucleic acid capable of directing expression of said protein of interest in said host cell
  transforming said host cell with the construct,
  cultivating the host cell, thereby obtaining expression of the GM-CSF and secretion of the GM-CSF into the culture medium,
  thereby obtaining culture medium comprising the GM-CSF.

The composition comprising GM-CSF and nucleic acids may thus in this embodiment of the invention be the culture medium or a composition prepared from the culture medium.

In another embodiment of the invention, said composition is an extract prepared from animals, parts thereof or cells or an isolated fraction of such an extract.

In an embodiment of the invention, the GM-CSF is recombinantly produced in vitro in host cells and is isolated from cell lysate, cell extract or from tissue culture supernatant. In a more preferred embodiment, the GM-CSF is produced by host cells that are modified in such a way that they express the relevant cytokine. In an even more preferred embodiment of the invention said host cells are transformed to produce and excrete the relevant GM-CSF.

Compositions according to the present invention may comprise 1 μg/g to 1000 μg/g GM-CSF or functional variants or homologues thereof, more preferably 10 μg/g to 300 μg/g GM-CSF or functional variants or homologues thereof.

Sucrose octasulfate (SOS) and sucralfate

The compositions of the present invention comprise SOS or a derivative thereof, such as for example sucralfate. SOS is a form of sucrose wherein all eight available hydroxyl groups are sulfated to form an acid compound. Though in the following description reference is made to SOS, it is understood that by this term is also meant salts of the acid normally present in a human or animal body, such as $Na^+$, $K^+$, $Mg^{2+}$ or $Ca^{2+}$ salts, and additionally salts of $Al_2(OH)^{5+}$.

Sucralfate is a form of SOS wherein each sulfated anion is salinized with the ion $Al_2(OH)^{5+}$. The chemical formula is 3,4,5,6-tetra-(polyhydroxyaluminum)-alpha-D-glucopyranosylsultate-2,3,4,5,-tetra-(polyhydroxyaluminum)-beta-D-fructofuranoside sulfate. Sucralfate is a known compound in therapeutic use (see for example "The Merck Index") and is marketed, for example, by the German firm BK GIULINI GmbH. Sucralfate has long been used in the prevention and treatment of gastric ulcer, duodenal ulcer, acute gastritis, symptomatic chronic gastritis, NSAID gastropathies, reflux esophagitis; compositions for this therapeutic use are marketed under various brand names (Martindale, The Complete Drug Reference, 34th edition, 2005). Sucralfate can function as a cytoprotective agent which adheres to mucoproteins and forms a protective barrier at wound sites. In oral form, it is used as ulcer medication, and as a topical preparation, it has been used to treat a variety of wounds. In a preferred embodiment of the present invention, pharmaceutical compositions of the present invention comprise sucralfate.

SOS and salts thereof including sucralfate are available from commercial sources such as Sigma-Aldrich and Santa Cruz biotechnology.

Without being bound by theory, SOS is believed to stimulate fibroblast growth factor (FGF) signaling by binding and stabilizing FGFs. It has been shown that SOS induces FGF-dependent dimerization of FGF receptors (FG-FRs) (Yeh et al., 2002). In addition, SOS can help increase the amount of collagen in the wound, form a cytoprotective barrier, increase mucus release in mucosal tissue, change ion transport and increase the release of prostaglandins. Additionally, SOS is capable of counteracting the matrix degeneration caused by the inflammatory reaction itself, or related to bacterial colonization or infection, by stimulating the content of wound collagen. Stimulation of collagen in a wound can be useful for decreasing or preventing scarring in relation to the healing.

The invention therefore concerns a composition comprising 5% w/w to 20% w/w of a suspension of SOS or a derivative or salt thereof in water, such as for example a suspension in double-distilled water, a buffered saline solution, a sterile physiological electrolyte solution or water for injection, or a suspension of SOS or a derivative or salt thereof in an HA hydrogel as described herein. Such suspensions according to the present invention comprises SOS or a derivative thereof at a concentration not higher than 20% w/w, and preferably 8-15% w/w, such as for example 8% w/w, or 9% w/w, or 10% w/w, or 11% w/w, or 12% w/w, or 15% w/w.

In a more preferred embodiment of the present invention, the composition comprises an SOS gel suspension at a concentration of essentially 10% w/w, and even more preferably, the composition comprises sucralfate at a concentration of essentially 10% w/w.

The compositions according to the present invention comprise GM-CSF or functional variants or homologues thereof, SOS or sucralfate, and hyaluronic acid (HA). These compounds may be mixed in various ratios according to the present invention. A typical composition according to the present invention may for example include an aqueous solution of HA at 0.01% w/w to 35% w/w with SOS at 8% w/w to 15% w/w and GM-CSF or functional variants or homologues thereof at 1 μg/g to 1000 μg/g, for example, such as an aqueous solution of HA at 0.1% w/w to 10% w/w with SOS at 10% w/w and GM-CSF or functional variants or homologues thereof at 100 μg/g.

Hyaluronic Acid (HA)

The compositions of the present invention comprise HA or a derivative thereof. Though in the following description reference is made to HA, it is understood that by this term are meant as well salts of the acid normally present in a human or animal body, such as $Na^+$, $K^+$, $Mg^{2+}$ or $Ca^{2+}$ salts.

HA is a generic name for heteroglycan polymers derived from the repetition of a structural unit comprising D-glucuronic acid and N-acetyl-D-glucosamine. HA is also known as hyaluronan or hyaluronate. HA, in the forms naturally occurring in many animal tissues, may have a molecular weight (MW) ranging from about 5,000 Da to about 20 million Da, and the properties of a specific sample of the compound may vary depending on its actual MW. HA is a known biodegradable and bioreabsorbable, highly hydrophilic polymer and is a fundamental component of the extracellular matrix (ECM). It is essential for numerous body tissues such as connective or epithelial tissues, and is present in the inner ear fluids, in the vitreous humor of the eyes and also in the synovial fluid of the joints.

Wound healing (in particular skin wound healing) is a complex process, and includes many interacting processes initiated by hemostasis and the release of platelet-derived factors. The following stages are inflammation, granulation tissue formation, re-epithelialization and remodeling. HA plays a multifaceted role in mediation of these cellular and matrix events.

The wound tissue in the early inflammatory phase of wound repair is abundant in HA, probably reflecting increased synthesis. It is known in the art that HA acts as a promoter of early inflammation, which is crucial to the whole skin wound-healing process. Additionally, HA is capable of moderating the inflammatory response, which may contribute to the stabilization of granulation tissue matrix. For example, HA has been observed to enhance cellular infiltration in the murine air pouch model of carrageenan/IL-1-induced inflammation. Other studies have demonstrated an HA dose-dependent increase of the proinflammatory cytokines TNF-α and IL-8 production by human uterine fibroblasts via a CD44-mediated mechanism. Endothelial cells, in response to inflammatory cytokines such as TNF-α and bacterial lipopolysaccharide, also synthesize HA, which has been shown to facilitate the primary adhesion of cytokine-activated lymphocytes expressing the HA-binding variants of CD44 under laminar and static flow conditions.

Granulation tissue is the perfused, fibrous connective tissue that replaces a fibrin clot in healing wounds. It typically grows from the base of a wound and is able to fill wounds of almost any size. HA is abundant in granulation tissue matrix, where it helps to produce a conductive environment for the migration of cells into this temporary wound matrix.

Although inflammation is an integral part of granulation tissue formation, the inflammation must subsequently be moderated for normal tissue repair to proceed. The initial granulation tissue formed is highly inflammatory with a high rate of tissue turnover mediated by matrix-degrading enzymes and reactive oxygen metabolites produced by the inflammatory cells. Stabilization of the granulation tissue matrix can be achieved by moderating inflammation. HA functions as an important moderator in this respect, in contrast to its initial role in inflammatory stimulation, as described above. The directed migration and control of the cell locomotor mechanisms are mediated via the specific cell interaction between HA and cell surface HA receptors.

The three principal cell surface receptors for HA are CD44, RHAMM, and ICAM-1. CD44 is the main cell surface receptor for HA. CD44 mediates cell interaction with HA and the binding of HA plays an important part in various physiologic events such as cell aggregation, migration, proliferation and activation, cell-cell and cell-substrate adhesion, and assembly of pericellular matrices from HA and proteoglycan. Endocytosis of HA leads to its degradation in macrophages. RHAMM is related to cell migration and forms links with several protein kinases associated with cell locomotion, for example, extracellular signal-regulated protein kinase (ERK), p125fak, and pp60c-src.

Furthermore, HA binds to TSG-6 (TNF-stimulated gene 6 protein) and may moderate inflammation and stabilize the granulation tissue as healing progresses by contributing to the formation of a stable complex with the serum proteinase inhibitor IαI (inter-α-inhibitor). The inhibition of inflammation decreases the plasmin activation of the proteolytic cascade of matrix metalloproteinases and other proteinases that damage inflammatory tissue.

HA also has crucial functions in the re-epithelialization process. It serves as an integral part of the extracellular matrix of basal keratinocytes, which are major constituents of the epidermis. It also has a free radical scavenging function and a role in keratinocyte proliferation and migration.

In normal skin, HA is found in relative high concentrations in the basal layer of the epidermis, where proliferating keratinocytes are found. Here it has the functions of maintaining the extracellular space and providing an open, hydrated structure for the passage of nutrients.

HA is a highly hydrophilic polymer, dissolving readily in water to form hydrogels.

In addition to the above-mentioned functions of HA in the healing process, a beneficial function of an HA hydrogel is to facilitate the adhesion of the composition to the site of treatment and thereby increase the exposure time of the treated tissue to the compounds of the composition.

The compositions of the present invention preferably comprise such hydrogels, which can, for example, be formed by dissolving a salt of HA in water, which can be double-distilled water, a buffered saline solution, a sterile physiological electrolyte solution or water for injection, in such an amount that its concentration in the resulting hydrogel is between 0.001% w/w (by weight) and 65% w/w, such as between 0.01% w/w and 35% w/w, or such as between 0.1% w/w and 10% w/w. These hydrogels are stable for long periods and can be stored for at least six months even at ambient temperature without altering their properties, in particular their viscosity.

HA is available from a number of commercial sources, for example Sigma-Aldrich, Novozymes and Hyalogic.

In one embodiment, a composition according to the present invention comprises HA at 1 μg/mL to 650 mg/mL, such as 10 μg/mL to 350 mg/mL, such as 5 μg/mL to 500 μg/mL, or such as 100 μg/mL to 100 mg/mL.

Further Ingredients of the Composition

Vitamin A and anti-oxidant agents may further have a stimulating effect on wound healing. In one embodiment of the present invention, the compositions as defined herein further comprise vitamin A and/or an anti-oxidant agent.

Medical Indications

It is an aspect of the present invention to provide a composition comprising GM-CSF or a functional variant or homologue thereof, SOS or sucralfate and HA for use in the treatment, prevention or alleviation of irritation or lesions such as wounds, chronic skin lesions and other lesions of the skin, mucous membranes or connective tissues of the body which may be acute or chronic. Such lesions may be caused by a broad spectrum of events and/or may be associated with other diseases. In one embodiment of the present invention, lesions to be treated or prevented by methods as defined herein include lesions associated with incision, lacerations, abrasions, blister, hematoma, puncture, penetration, gunshot, electricity, irradiation, chemical, trauma, crush, bite, burn, frost, surgery (for example in non-mucosal tissue, such as for example neurosurgery on the scalp, peritoneal surgery, transplantation surgery, orthopedic surgery, and/or surgery in mucosal tissue such as gingival, urinary, bladder or anal surgery), primary cancer or metastasis, benign tumor, acne, infections such as fungal (for example with different forms of *Candida*), viral (for example with different forms of herpes) and/or bacterial infections, or other infectious conditions such as for example osteomyelitis, staphylococcal infection (such as for example with *Staphylococcus aureus*), infection with beta-hemolytic streptococci, infection with *Pseudomonas aeruginosa*, lesions associated with decreased circulation of blood, such as venous leg ulcers associated with decreased venous valve function, venous foot ulcers, arterial leg ulcers, arterial foot ulcers, decubitus ulcers, pressure lesions, or bedsores, lesions associated with diabetes, lesions associated with local poisoning and lesions associated with aspiration of gastric content into the lungs, pulmonary aspiration and/or esophagitis.

Chronic or "non-healing" wounds, lesions or ulcers arise when a wound generally fails to follow an appropriate timely healing process to achieve the normal sustained and stable anatomic and functional integrity of healed tissue. Generally speaking, a skin lesion which has failed to make at least substantial progress towards healing within a period of at least about three months, or which has become stable in a partially healed state for more than about three months, or a skin lesion which is unhealed after at least about six months is categorized as a chronic or non-healing wound.

Malignant or pre-malignant non-healing ulcerous skin lesions may arise in connection with a primary cancer of the skin, or with a metastasis to the skin from a local tumor or from a tumor in a distant site. They may be draining or non-draining. They may, for example, take the form of a cavity, an open area on the surface of the skin, skin nodules, or a nodular growth extending from the surface of the skin.

Benign non-healing ulcerous skin lesions are not associated with cancer, and include venous leg ulcers, venous foot ulcers, diabetic leg ulcers, diabetic foot ulcers, arterial leg ulcers, arterial foot ulcers, decubitus ulcers (e.g. pressure sores, bedsores), post-surgical ulcerous lesions and chronic burn lesions. They may, for example, take the form of a cavity, an open area on the surface of the skin, skin nodules, or a nodular growth extending from the surface of the skin. Typically, they comprise an open granulating area on the surface of the skin.

In one embodiment of the present invention, the compositions and methods of the present invention are used for the treatment or pre-emptive therapy of lesions showing early signs of developing into non-healing ulcerous skin lesions.

Exudate management can be a difficult task for the caring professional attending to a patient suffering from a chronic ulcerous lesion. A balance needs to be struck between the desire to remove exudate to maintain the patients quality of life at as high a level as possible, and maintenance of an appropriate level of fluid to prevent the lesion becoming too dry or too wet. In one embodiment of the present invention, the composition is a hydrogel which comprises a combination of HA, SOS or sucralfate and GM-CSF and thereby provides moisture to the healing wound, ulcer or other type of skin lesion, in order to facilitate the healing process.

Prevention may be equivalent to reducing risk of the development of symptoms associated with irritation or lesions of the skin, mucosal membranes or connective tissue of the body, such as for example reducing the risk of symptoms of inflammation, proliferation, and maturation phases of the healing process and/or symptoms of chronic ulcerous skin lesions.

Lesion such as wounds, ulcers and other lesions of the skin, mucous membranes or connective tissue may be prone to infection by bacteria, fungi or viruses because of disruption of the protective barriers of the skin or mucosa. This results in further tissue damage and may prolong wound healing by promoting more inflammation. The symptoms of infection are increased or sustained pain, redness or swelling, pus discharge, bad odor or non-healing of the wound. The most common bacteria causing wound infection is *Staphylococcus aureus* and other groups of staphylococci, beta-hemolytic streptococci, and *Pseudomonas aeruginosa*. Contamination from other parts of the body may also cause wound infection. In one embodiment of the present invention, compositions as defined herein are used for preventing, treating or alleviating lesions or wounds associated with infection and/or inflammation caused by infection, by modulating the immune response. Such an infection and/or inflammation caused by infection may include a fungal, viral and/or bacterial infection as specified above.

GM-CSF when used alone has shown some efficacy in the healing of diabetic wounds. In a preferred embodiment of the present invention, the composition comprising GM-CSF or a functional variant or homologue thereof, HA and SOS or sucralfate may also be used in the pre-emptive treatment, alleviation of signs and symptoms, or treatment of irritation, lesions and wounds in a diabetic subject, whether suffering from type 1 or type 2 diabetes mellitus.

The diabetic chronic skin lesions are accompanied by other signs and symptoms apart from the failure of the normal healing process. Typical accompanying symptoms of non-healing ulcerous skin lesions include one or more of the features of pain, exudation, malodor, excoriation, spreading of the wound, tissue necrosis, irritation and hyperkeratosis. Such features can be extremely debilitating and embarrassing for the patient, and can seriously harm the patient's quality of life. In severe cases, they may lead to limb amputation or even death. The compositions and methods of the present invention are useful for treating and preventing non-healing ulcers accompanied by these features.

Preemptive treatment and/or alleviation of clinical of signs and symptoms obtained by the use of the compositions of the present invention can be evaluated by measuring the positive changes in factors describing the healing of a wound or lesion, such as decreased healing time, altered duration of various phases of the healing process, decreased size, altered shape, decreased depth, and altered edges and base of the wound, amount and quality of the granulation tissue, and/or type of discharge of the treated tissue, increased extracellular matrix, increased collagen content, increased angiogenesis, and/or biopsy derived variables such as immunohistochemical examination, surveillance cultures, and systemic markers of inflammation, specific or unspecific antibodies and surrogate markers of $T_H2$ and/or $T_H1$ immune responses or changes in expression of cytokines.

In one embodiment of the present invention, the subject treated with a composition of the present invention is a mammal. In a further embodiment, the mammal is a human.

In one embodiment, the human is a child younger than 15 years of age. In one embodiment, the human is an adult 15 years of age or older.

Age is known to be a factor that reduces the healing abilities of the skin and mucous membranes. In one embodiment of the present invention, the compositions and methods provided herein are for the treatment and prevention of age-related impairment of healing of lesions and wounds, such as in a human adult aged 50 years or more.

Other Treatments

In one embodiment of the invention, the compositions are used for the treatment of scars or for the prevention of scar formation, such as keloid scars, post-burn scars, scarring tissue after trauma, and post-surgical scarring.

Formulations

Pharmaceutical compositions or formulations for use in the present invention include GM-CSF or functional variants or homologues thereof, HA and SOS. Such compositions or formulations may preferably be dissolved in a pharmaceutically acceptable carrier, preferably an aqueous carrier or diluent. A variety of aqueous carriers may be used, including, but not limited to 0.9% saline, buffered saline, physiologically compatible buffers and the like. The compositions may be sterilized by conventional techniques well known to those skilled in the art. The resulting aqueous solutions may be packaged for use or filtered under aseptic conditions and freeze-dried, the freeze-dried preparation being dissolved in a sterile aqueous solution prior to administration. In one embodiment, a freeze-dried preparation comprising GM-CSF or functional variants or homologues thereof, HA and SOS may be pre-packaged for example in single dose units.

The composition of the present invention may be in the form of a powder, paste, paint, ointment, lotion, gel, cream, salve, emulsion, suspension, solution, spray, sponge, strip, plaster, pad, dressing, or formulated in an ostomy plate. Such formulations may further comprise one or more ingredients which are commonly used in wound treatment formulations, such as selected from the group comprising water, glycerin-based, non-adherent, cross-linked polymer, glycerin, co-polymer, propylene glycol, humectant, calcium and/or sodium salts of alginic acid, non-woven composites of fibers, silver, vitamin A and/or other anti-oxidant agents and honey.

The compositions according to the present invention are formulated so as to allow the active ingredients to pass the epidermal or transmucosal barrier in order to reach the white blood cell targets of the GM-CSF, i.e. the macrophages and/or the granulocytes, because these cells represent the cellular local host defense effectors. For such applications, the compositions according to the present invention may be formulated for improved passage across the transmucosal barrier or epidermis.

Improved passage over said barriers may be obtained by a formulation which is capable of adhering to the mucosa, epidermis, or wound surface, such as for example a gel, paste, ointment, lotion, cream or salve.

The compositions may contain pharmaceutically acceptable auxiliary substances or adjuvants, including, without limitation, pH-adjusting and buffering agents and/or tonicity adjusting agents, such as for example sodium acetate, sodium lactate, sodium chloride, potassium chloride, calcium chloride, etc.

Compositions according to the present invention may comprise GM-CSF or a fragment or variant thereof formulated in a liposome with an outer fatty layer with a core of water phase in which the active substance is dissolved. The lipid-component of such formulations overcomes the penetration barrier of the epidermis and mucous membranes.

The formulations may comprise pharmaceutically acceptable carriers and excipients including microspheres, liposomes, microcapsules, nanoparticles or the like. Conventional liposomes are typically composed of phospholipids (neutral or negatively charged) and/or cholesterol. The liposomes are vesicular structures based on lipid bilayers surrounding aqueous compartments. They can vary in their physiochemical properties such as size, lipid composition, surface charge and number and fluidity of the phospholipids bilayers. The most frequently used lipid for liposome formation are: 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), 1,2-dimyristoyl-sn-glycero-3-phosphoethanolamine (DMPE), 1,2-dipalmitoyl-sn-glycero-3-phosphoethanolamine (DPPE), 1,2-dioleoyl-sn-glycero-3-phosphoethanolamine (DOPE), 1,2-dimyristoyl-sn-glycero-3-phosphate (monosodium salt) (DMPA), 1,2-dipalmitoyl-sn-glycero-3-phosphate (monosodium salt) (DPPA), 1,2-dioleoyl-sn-glycero-3-phosphate (monosodium salt) (DOPA), 1,2-dimyristoyl-sn-glycero-3-[phospho-rac-(1-glycerol)] (sodium salt) (DMPG), 1,2-dipalmitoyl-sn-glycero-3-[phospho-rac-(1-glycerol)] (sodium salt) (DPPG), 1,2-dioleoyl-sn-glycero-3-[phospho-rac-(1-glycerol)] (sodium salt) (DOPG), 1,2-dimyristoyl-sn-glycero-3-[phospho-I-serine] (sodium salt) (DMPS), 1,2-dipalmitoyl-sn-glycero-3-[phospho-I-serine) (sodium salt) (DPPS), 1,2-dioleoyl-sn-glycero-3-[phospho-I-serine] (sodium salt) (DOPS), 1,2-dioleoyl-sn-glycero-3-phosphoethanolamine-n-(glutaryl) (sodium salt) and 1,1',2,2'-tetramyristoyl cardiolipin (ammonium salt). Formulations composed of DPPC in combination with other lipids or modifiers of liposomes are preferred, e.g. in combination with cholesterol and/or phosphatidylcholine.

A useful way of producing liposomes is to attach the hydrophilic polymer polyethylene glycol (PEG) covalently to the outer surface of the liposome. Some of the preferred lipids are: 1,2-dipalmitoyl-sn-glycero-3-phosphoethanolamine-n-[methoxy(polyethylene glycol)-2000] (ammonium salt), 1,2-dipalmitoyl-sn-glycero-3-phosphoethanolamine-n-[methoxy(polyethylene glycol)-5000] (ammonium salt), 1,2-dioleoyl-3-trimethylammonium-propane (chloride salt) (DOTAP).

Possible lipids applicable for liposome production are supplied by e.g. Avanti, Polar Lipids, Inc., Alabaster, AL Additionally, the liposome suspension may include lipid-protective agents which protect lipids against free-radical and lipid-peroxidative damage on storage. Lipophilic free-radical quenchers, such as alpha-tocopherol and water-soluble iron-specific chelators, such as ferrioxamine, are preferred.

A variety of methods are available for preparing liposomes, as described by e.g. Szoka et al. (1980) and U.S. Pat. Nos. 4,235,871, 4,501,728 and 4,837,028, all of which are incorporated herein by reference. Another method produces multi-lamellar vesicles of heterogeneous sizes. In this method, the vesicle-forming lipids are dissolved in a suitable organic solvent or solvent system and dried under vacuum or in an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the drug and its targeting component and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

Micelles are formed by surfactants (molecules that contain a hydrophobic portion and one or more ionic or otherwise strongly hydrophilic groups) in aqueous solution.

Common surfactants well known to those of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127 (Wyandotte Chemicals Corp.). Preferred surfactants are nonionic polyoxyethylene and polyoxypropylene detergents compatible with intravenous injection, such as Tween 80, PLURONIC F-68, n-octyl-beta-D-glucopyranoside and the like. In addition, phospholipids, such as those described for use in the production of liposomes, can also be used for micelle formation.

The pH value of the compositions and formulation according to the present invention may be adjusted to a pH of between 3 and 10; such as between 4 and 9; such as between 4 and 8; such as between 4 and 8; such as between 5 and 8; such as between 6 and 8: preferably between 6.5 and 7.5 such as wherein said composition has a pH of about 7.

In one embodiment, a freeze-dried preparation of a composition according to the present invention may be pre-packaged, for example in single dose units. In an even more preferred embodiment the single dose unit is a first composition which may be a preparation of HA and SOS, for example comprising a hydrogel of HA, SOS and water (added as double-distilled water, buffer solution or physiological solution) and one or more other compositions comprising GM-CSF or functional variants or homologues thereof, and/or other active ingredients.

In the case of using the composition as a kit, a bioactive hydrogel may be produced just before its use by mixing in the desired ratio the hydrogel of the HA and SOS with GM-CSF or functional variants or homologues thereof and shortly after its preparation applying the mixture to the tissue in need of treatment.

Administration

The compositions and methods of the present invention are useful for the treatment or prevention of wounds, ulcers, scars and other lesions of the skin or mucous membranes of the body, and may be applied by administration methods conventionally used in the art for topical application of preparations to the skin or mucous membranes of an individual animal or human, including the lining of body cavities. "Topical administration" is defined as the delivery of the therapeutic agent to the surface of the wound, lesion or scar and adjacent tissue. Such topical administration may for example include the topical application of a composition by massage, injection, spraying, brushing, application of a patch, powder, paste, ointment, lotion, gel, cream, salve, emulsion, suspension, solution, sponge, strip, plaster, pad, dressing, or an ostomy plate or other methods normally used for topical administration.

The epidermis sometimes presents a barrier that prevents the components or compositions of the present invention from reaching the intracutaneous and subcutaneous layers of the skin and exerting their effects there. Many wounds, ulcers and/or scars could be treated more effectively and with fewer adverse effects if the active agents used for treatment could be more efficiently delivered to the underlying tissues, such as for example the tissues underlying the epidermis, in a reproducible manner. The efficiency of penetration of therapeutic agents into the deeper tissues may require penetrating technologies that bypass the barriers of the mucosa, skin or necrotic tissue. Such penetrating technologies are useful for depositing the compositions of the present invention under the stratum corneum or epidermis of the skin, such as into the intracutaneous or subcutaneous layers of the skin, and such penetrating technologies can be useful for improving the distribution of the compositions of the present invention in different layers of the skin and thereby decrease the concentration gradient of the components of said compositions from the cutaneous surface to the subcutaneous tissues.

It is an aspect of the present invention to provide penetrating technologies that bypass the tissue barriers mentioned, thereby facilitating the local transport of active ingredients or components of the compositions of the present invention to the different zones of the treated tissues, such as for such as for example deeper dermal tissue underlying the epidermal surface barrier. In one embodiment of the present invention, the compositions of the invention are deposited in the skin layers under the epidermis, such as the dermis, or the subcutaneous layers constituting the hypodermis.

The composition according to the invention may be applied by use of devices which are useful for such application, such as a roller tool for transmucosal or transepidermal administration as described herein. The roller tool consists essentially of a spiked roller, as illustrated by FIG. 1. The length of the cylindrical component is 2-5 cm and its diameter is 2-3 cm. The roller can be pushed by means of a removable U-shaped handle to which an optional extension can be attached. The roller body and handle are made of materials that are resistant to sterilization by autoclaving or chemical means, such as stainless steel, surgical titanium alloy, polypropylene or polycarbonate. The roller surface that contacts the lesion is equipped with firmly attached sharp spikes or pins of base diameter 300-400 µm, capable of penetrating the epidermis or mucosa. The density of these pins or spikes is approximately 25 per $cm^2$ of roller contact surface. The spikes are of identical length in an individual roller body. Roller bodies with different lengths of spike can be interchanged on the handle. The spikes are made of stainless steel that is resistant to sterilization. Their length may be 0.1 mm to 3 mm, preferably 0.70 mm to 1.2 mm. Without being bound by theory, it is believed that the length of the spikes may ensure the application of compositions of the present invention in different layers of the skin, and in this way provide beneficial effects of the treatment. Table 1 shows an overview of the lengths of the spikes and respective effects of the treatment.

TABLE 1

Length of spikes and effect on Immuno-inflammation

| Length of spikes | Goal of drug deposition | Effect on inflammation |
| --- | --- | --- |
| 0.1-0.5 mm | Intracutaneous (i.c.) | $T_H1$ |
| 0.7-1.0 mm | Subcutaneous (s.c.) | Mixed $T_H1$ and $T_H2$ |

NB: $T_H1$: type-1 T-helper cells; $T_H2$: type-2 T-helper cells. These are involved in different immuno-inflammatory responses.
The spikes can be shorter for deposition in areas of thin skin, e.g. the face, or longer for deposition in areas of thicker skin, e.g. the palms and soles.

In one embodiment of the present invention, the roller tool may further comprise a substantially semi-cylindrical sleeve connected to the U-shaped handle.

The roller tool may comprise a reservoir system for the administration of pharmaceutical compositions according to the invention. In such an embodiment, the spikes of the cylindrical roller body are of the nature of hollow hypodermic needles that allow a pharmaceutical composition to pass from the interior of the roller body to be delivered to the tissue through the hollow spikes.

An example of a reservoir system for pharmaceutical compositions according to the invention comprises an enclosed external reservoir for the pharmaceutical composition that can be attached to the handle and having an outlet that connect via an exit hose connecting to conduits delivering the compositions to the interior of the cylinder.

Another example of a reservoir system for the pharmaceutical compositions is an internal reservoir system for the pharmaceutical composition within the cylindrical roller body.

In one embodiment, the rolling tool as described herein is preferably used for application of the compositions of the present invention on intact skin or scarring tissue.

Laser perforation is another method by which the wound surface or epidermis can be perforated by a number of small holes, such as for example about 4000 holes per cm$^2$. Laser perforation may be used for example for the localized administration of the compositions of the present invention in a limited area such as in a cancer of the skin, which may be a spinocellular cancer or a basal cell carcinoma. In one embodiment of the present invention, the compositions of the present invention are administered by topical administration as defined herein in combination with laser perforation.

In one embodiment, the administration of the compositions of the present invention is by injection, or by topical administration as mentioned herein in combination with other methods for penetration though the surface, such as laser perforation or a roller tool as defined herein. This technique and the perforating techniques previously described may be used before, during or after the topical administration of the compositions of the invention.

Finally, a method for enhancing the transcutaneous transportation of the active ingredients of the compositions of the invention is the application of a skin ointment, such as a plant extract, which reduces the transdermal resistance toward each of the three components SOS, HA & GM-CSF.

Dose

By "effective amount" of the compositions of the present invention is meant a dose, which, when administered to a subject in need thereof, achieves a concentration which has a beneficial biological effect in the treatment, prevention or alleviation of irritation or lesions such as wounds, ulcers and other lesions or scars of the skin, mucous membranes or connective tissues of the body. Such an effective amount may be determined by a patient's attending physician or an affected animal's veterinarian and is readily ascertained by one of ordinary skill in the art. Factors which influence what a therapeutically effective amount will be include, the specific activity of the therapeutic agent being used, the lesion type (mechanical or thermal, full or partial thickness, etc.), the size of the lesion, the depth of the lesion (if full thickness), the absence or presence of infection, the time elapsed since the infliction of the injury, and the age, physical condition, disease status and nutritional status of the patient. Additionally, other medication that the patient may be receiving will affect the determination of the therapeutically effective amount of the composition to be administered.

GM-CSF or a functional variant or homologue thereof may be administered in an effective amount defined in terms of cm$^2$ of wound area to be treated, such as from between 10 μg to 100 μg per cm$^2$.

In practical terms, a pharmaceutical composition of the present invention comprises GM-CSF or a fragment or variant thereof at a concentration in the range of 1 μg/g to 1000 μg/g, such as in the range of 5 μg/g to 500 μg/g, or such as in the range of 10 μg/g to 300 μg/g.

Each dose can be administered once a day, twice a day, three times a day, four times a day, five times a day or six times a day.

Duration of dosing will typically range from 1 day to about 4 months, such as in the range of 1 day to 2 days, for example 2 days to 3 days, such as in the range of 3 days to 4 days, for example 4-5 days, such as 5-6 days, for example 6-7 days, for example 7-14 days, such as one week to two weeks, for example two to four weeks, such as one month to two months, for example 2 to 4 months, or as long as the lesion remains unhealed.

The transformation of a resting macrophage into a fully immunocompetent dendritic cell after in vitro incubation of macrophages with GM-CSF takes approximately 10 days. In one embodiment, a duration of a dose has the length allowing for said transformation. Thus the duration can be 7-14 days, such as 8-12 days, for example 8 days, or for example 9 days, or for example 10 days, or for example 11 days, or for example 12 days.

A dose regime may alternate between periods of administration of the composition according to the present invention and periods without administration (a pause in treatment). A period with a pause in treatment in such a dose regime may last 5-10 days, for example 5 days, or for example 6 days, or for example 7 days, or for example 8 days, or for example 9 days or for example 10 days or more, for example 1 to 4 months.

Examples of dosage regimens may include a cycle of 10 days' treatment with the composition according to the present invention and 7 days' pause of treatment.

The conversion of resting macrophages (MF) into dendritic (DC) cells may be boosted by repeating a dosage regimen. Thus, dosage regimens can be repeated once, twice, three times, four times, five times or more in order to obtain an effective treatment.

In one embodiment, a dosage regimen is repeated, such as once, twice, three times or more, for example repeated for the rest of the lifespan of a subject in need.

In another embodiment, patients are treated with a dosage regimen of 10 days' treatment with a composition according to the present invention, followed by 7 days pause in said treatment and subsequently repeating the dosage regimen 2-3 or more times.

In embodiments where the compositions comprise SOS, the composition according to any one of the preceding embodiments may comprise SOS at a concentration of 50 mg/g to 200 mg/g.

The composition according to any one of the preceding embodiments may comprise a suspension of SOS or sucralfate of 8% w/w to 15% w/w.

The composition according to any one of the preceding embodiments may comprise an aqueous solution of HA at a concentration of 0.01% w/w to 35% w/w, with SOS at a concentration of 8% w/w to 15% w/w and GM-CSF or functional variants or homologues thereof at a concentration of 1 μg/g to 1000 μg/g.

The composition according to any one of the preceding embodiments may comprise an aqueous solution of HA at a concentration of 0.01% w/w to 35% w/w, with SOS at a concentration of 8% w/w to 12% w/w and GM-CSF or functional variants or homologues thereof at a concentration of 5 μg/g to 500 μg/g.

The composition according to any one of the preceding embodiments may comprise an aqueous solution of HA at a concentration of 0.1% w/w to 10% w/w, with SOS at a concentration of 10% w/w and GM-CSF or functional variants or homologues thereof at a concentration of 20 μg/g to 300 μg/g.

Methods of Treatment

The present invention provides a method for the treatment, prevention or alleviation of irritation or lesions such as wounds, ulcers and other lesions of the skin, mucous membranes or connective tissues of the body, which comprises at least one step of administering to the subject an effective amount of a composition according to the present invention comprising GM-CSF or a fragment or variant thereof, SOS or sucralfate and HA.

In a method of treatment according to the present invention, the compounds GM-CSF, SOS or sucralfate and HA may be administered to a subject sequentially or simultaneously by methods for topical administrations as defined herein.

In one embodiment of the present invention, the composition as defined herein is applied by means of a roller tool as provided herein.

The methods for treatment, prevention or alleviation of irritation or lesion such as wounds, ulcers and other lesions of the skin, mucous membranes or connective tissues of the body according to the present invention may include the administration of compositions as defined herein during or after surgery.

In one embodiment of the present invention, the methods for prevention, alleviation and/or treatment of the present invention include a step of treating the tissue in need of treatment with a local anesthetic agent, such as for example lidocaine.

In methods of the present invention, the treatments with a composition as defined herein may be combined with other types of treatment or procedures normally used in the treatment of wounds, ulcers, scars or other lesions, such as for example debridement, surgical wound revision, topical negative pressure treatment (TNPT), frequent change of wound dressing, control of diabetes and/or off-loading in order to reduce edema.

The co-administration of bactericidal or antifungal agents may further facilitate the treatments according to the present invention by preventing or treating infections in wounds, ulcers or other injured sites. In one embodiment of the present invention, the composition s is co-administrated with one or more antibacterial and/or antifungal agents. Such antibacterial and/or antifungal agents may be administered systemically or topically. Such co-treatment does not interfere with the treatment using the composition of the present invention because the administration of GM-CSF enhances the local host defense.

Surveillance culture (for detecting infections) is highly recommended to identify the contamination of a wound by microorganisms.

Embodiments

1. A composition comprising:
   a) granulocyte-macrophage-colony stimulating factor (GM-CSF) or a fragment or variant thereof, and
   b) sucrose octasulfate (SOS) or a salt thereof, such as sucralfate, and
   c) hyaluronic acid (HA).
2. The composition according to embodiment 1 for use as a medicament.
3. The composition according to embodiment 1 for use in the treatment, prevention or alleviation of irritation or lesions such as wounds, ulcers, scars and other lesions of the skin, mucous membranes or connective tissues of the body.
4. The composition according to any one of the previous embodiments for the treatment, prevention or alleviation of wounds and/or ulcers.
5. The composition according to any one of the previous embodiments wherein the wound and/or ulcer is non-healing.
6. The composition according to embodiments wherein the wound and/or ulcer is acute.
7. The composition according to embodiments 1 to 4 wherein the ulcers are non-healing ulcerous skin lesions.
8. The composition according to any one of the previous embodiments wherein the wound and/or ulcer is associated with an infection such as a fungal, viral and/or bacterial infection.
9. The composition according to any one of the previous embodiments, wherein the wound and/or ulcer is associated with diabetes mellitus.
10. The composition according to any one of the previous embodiments, wherein the wound and/or ulcer is associated with decreased circulation of blood, such as a venous leg ulcer, venous foot ulcer, arterial leg ulcer, arterial foot ulcer, or a decubitus ulcer.
11. The composition according to any one of the previous embodiments, wherein the wound and/or ulcer is associated with incision, lacerations, abrasions, blister, hematoma, puncture, penetration, gunshot, electricity, irradiation, chemical, trauma, crush, bite, burn, frost, surgery (for example in non-mucosal tissue, such as for example neurosurgery on the scalp, peritoneal surgery, transplantation surgery, orthopedic surgery, and/or surgery in mucosal tissue such as gingival, urinary, bladder or anal surgery), primary cancer or metastasis, benign tumor, acne, infections such as fungal (for example with different forms of *Candida*), viral (for example with different forms of herpes) and/or bacterial infections, or other infectious conditions such as for example osteomyelitis, staphylococcal infection (such as for example with *Staphylococcus aureus*), infection with beta-hemolytic streptococci, infection with *Pseudomonas aeruginosa*, lesions associated with decreased circulation of blood, such as venous leg ulcers associated with decreased venous valve function, venous foot ulcers, arterial leg ulcers, arterial foot ulcers, decubitus ulcers, pressure lesions, or bedsores, lesions associated with diabetes, lesions associated with local poisoning and lesions associated with aspiration of gastric content into the lungs, pulmonary aspiration and/or esophagitis.
12. The composition according to any one of the previous embodiments, wherein said composition formulated as a powder, paste, paint, ointment, lotion, gel, cream, salve, emulsion, suspension, solution, spray, sponge, strip, plaster, pad, dressing, or formulated in an ostomy plate.
13. The composition according to any one of the preceding embodiments, wherein the composition is formulated as a gel.
14. The composition according to any one of the preceding embodiments, wherein the GM-CSF is in a liposomal or micelle, microcapsule or nanoparticle formulation.
15. The composition according to any one of the preceding embodiments wherein the GM-CSF variant is at least 70% identical to SEQ ID NO:1 or SEQ ID NO:2.
16. The composition according to any one of the preceding embodiments wherein the amino acid sequence of said GM-CSF comprises the amino acid sequence set forth in SEQ ID NO:2 or an amino acid sequence which is at least 70% identical to the sequence set forth in SEQ ID NO:2, such as at least 85% identical to the sequence set forth in SEQ ID NO:2, for example at least 90% identical to the sequence set forth in SEQ ID NO:2, such as at least 95% identical to the sequence set forth in SEQ ID NO:2, for example at least 97% identical to the sequence set forth in SEQ ID NO:2, such as at least 98% identical to the sequence set forth in SEQ ED NO:2, for example at least 99% identical to the sequence set forth in SEQ ID NO:2.
17. The composition according to any one of the preceding embodiments wherein the amino acid sequence of said GM-CSF consists of the amino acid sequence set forth in SEQ ID NO:2 or an amino acid sequence which is at least 70% identical to the sequence set forth in SEQ ID NO:2, such as at least 85% identical to the sequence set forth in SEQ ID NO:2, for example at least 90% identical to the sequence set forth in SEQ ID NO:2, such as at least 95% identical to the sequence set forth in SEQ ID NO:2, for example at least 97% identical to the sequence set forth in SEQ ID NO:2, such as at least 98% identical to the sequence set forth in SEQ ID NO:2, for example at least 99% identical to the sequence set forth in SEQ ID NO:2.

18. The composition according to any one of the preceding embodiments wherein said GM-CSF is a functional homologue or analogue of a native human GM-CSF, wherein (a) at least one amino acid of a pair of adjacent arginine amino acids occouring in said GM-CSF is substituted with a non-basic amino acid; and (b) said functional homologue or analogue of a native human GM-CSF displays biological activity in a human bone marrow assay.

19. The composition according to any one of the preceding embodiments wherein said GM-CSF is a variant of the amino acid sequence set forth in, wherein (a) at least one amino acid of a pair of adjacent arginine amino acids occouring in said GM-CSF is substituted with a non-basic amino acid; and (b) said functional homologue or analogue of a native human GM-CSF displays biological activity in a human bone marrow assay.

20. The composition according to any one of the preceding embodiments wherein said GM-CSF is a functional analogue of a native human GM-CSF having the sequence set forth in SEQ ID NO: 2, wherein Thr in position 98 (corresponding to position 115 of SEQ ID NO:1) is substituted with Ile.

21. The composition according to any one of the preceding embodiments wherein said GM-CSF is a functional analogue of a native human GM-CSF having the sequence set forth in SEQ ID NO: 2, wherein Ile in position 100 (corresponding to position 117 of SEQ ID NO:1) is substituted with Thr.

22. The composition according to any one of e preceding embodiments wherein the GM-CSF fragment comprises at least 50 contiguous amino-acid residues of any one of SEQ ID NO:1 or SEQ ID NO:2, such as at least 100 contiguous amino-acid residues of any one of SEQ ID NO:1 or SEQ ID NO:2.

23. The composition according to embodiment 22, wherein the fragment is at least 70% identical to SEQ ID NO:1 or SEQ ID NO:2 in the range of overlap.

24. The composition according to any one of the preceding embodiments, comprising GM-CSF at a concentration of 1 µg/g to 1000 µg/g.

25. The composition according to any one of the preceding embodiments, comprising GM-CSF at a concentration of 10 µg/g to 300 µg/g.

26. The composition according to any one of the preceding embodiments, comprising hyaluronic acid at a concentration of 0.01 mg/g to 650 mg/g.

27. The composition according to any one of the preceding embodiments, comprising hyaluronic acid at a concentration of 100 µg/g to 100 mg/g.

28. The composition according to any one of the preceding embodiments, wherein the form of sucrose octasulfate is sucralfate.

29. The composition according to any one of the preceding embodiments, comprising sucrose octasulfate or sucralfate at a concentration of 50 mg/g to 200 mg/g.

30. The composition according to any one of the preceding embodiments, comprising sucrose octasulfate or sucralfate at a concentration of 80 mg/g to 1500 mg/g.

31. The composition according to any one of the preceding embodiments, comprising a suspension of sucrose octasulfate or sucralfate at a concentration of 5% w/w to 20% w/w.

32. The composition according to any one of the preceding embodiments, comprising a suspension of sucrose octasulfate or sucralfate at a concentration of 8% w/w to 15% w/w.

33. The composition according to any one of the preceding embodiments comprising an aqueous solution of hyaluronic acid at a concentration of 0.01% w/w to 35% w/w with sucrose octasulfate at a concentration of 8% w/w to 15% why and GM-CSF or a functional variant or homologue thereof at a concentration of 1 µg/g to 1000 µg/g.

34. The composition according to any one of the preceding embodiments comprising an aqueous solution of hyaluronic acid at a concentration of 0.1% w/w to 10% w/w with sucrose octasulfate at a concentration of 10% w/w and GM-CSF or a functional variant or homologue thereof at a concentration of 20 µg/g to 300 µg/g.

35. The composition according to any one of the preceding embodiments further comprising vitamin A and/or an anti-oxidant agent.

36. The composition according to any one of the preceding embodiments, wherein the GM-CSF comprises a GM-CSF variant in the form of a conjugate capable of prolonging half-life of the GM-CSF.

37. The composition according to embodiments 28, wherein the conjugate capable of prolonging half-life of the active ingredient is albumin or a fatty acid.

38. The composition according to any one of the preceding embodiments wherein the composition has a pH of between 3 and 10; such as between 4 and 9; such as between 4 and 8; such as between 4 and 8; such as between 5 and 8; such as between 6 and 8; preferably between 6.5 and 7.5 such as a pH of about 7.

EXAMPLES

The following non-limiting examples further illustrate the present invention.

Example 1: Sequences

```
-Human pre-GM-CSF
>sp|P04141|CSF2_HUMAN Granulocyte-macrophage
colony-stimulating factor OS = Homo sapiens
                                    SEQ ID NO: 1
MWLQSLLLLGTVACSISAPARSPSPSTQPWEHVNAIQEARRLLNLSRDTAA
EMNETVEVISEMFDLQEPTCLQTRLELYKQGLRGSLTKLKGPLTMMASHYK
QHCPPTPETSCATQIITFESFKENLKDFLLVIPFDCWEPVQE -mature human GM-CSF
>sp|P04141|18-144
                                    SEQ ID NO: 2
APARSPSPSTQPWEHVNAIQEARRLLNLSRDTAAEMNETVEVISEMFDLQE
PTCLQTRLELYKQGLRGSLTKLKGPLTMMASHYKQHCPPTPETSCATQIIT
FESFKENLKDFLLVIPFDCWEPVQE
```

Example 2

Protocol for Testing a Composition on Chronic Wounds

1. Surgical cleaning of wound with removal of debris and necrotic tissue. If the final result is a clean wound and the patient is without signs of infection, systemic and/or local antibiotic (AB) is omitted. If signs and symptoms of infection are present, e.g. as detected by culture surveillance or as monitored by fever and inflammation markers (C-reactive protein (CRP) and procalcitonin (PCT)), the patient is a candidate for local or systemic AB treatment.

2. Administration of a composition of the invention. The epidermis is a barrier to the active ingredients reaching the target tissues, which are optimally the intracutaneous and subcutaneous layers of the skin.
 a) Application of the drug.
 Initially, a local anesthetic ointment is applied, e.g. a 0.9% aqueous solution of lidocaine or EMLA cream using an occlusive Band-Aid, applied at least one hour before the skin permeation maneuver.
 b) In order to administer compositions of the invention to the intracutaneous or subcutaneous tissues, the epidermal barrier needs to be penetrated by the "hedge-hogging" maneuver, by using e.g. the spiked roller with a spike length of between 0.1 mm and 1 mm.
 c) Application, dose and length of therapy (LOT).
 d) The most frequent form of application is a gel form of the composition of the invention. This is applied to the area of the skin with perforations.
 e) If the area of interest (AOI) is less than 5 cm$^2$, 1 mL of the composition is sufficient. If the AOI is larger, 2 mL or more are applied to obtain a fully covered area. It is desirable that at least a minimum thickness of 1 mm of the composition of the invention is applied to the AOI.
 f) The area which is covered with the composition is then covered with an occlusive Band-Aid, (such as Coloplast). The Band-Aid is left on the area for at least 4 h in order to ensure maximal intra- or subcutaneous deposition of the components.
 g) Both the wound periphery (edge) and the wound bed will be penetrated by the method.
 h) The above-mentioned procedure is maintained on a daily basis for at least 10 days in order to achieve the following effects: i) immunoinflammatory effects (TH2 to TH1 subset conversion) and ii) enhancing the formation of dendritic cells.

3. Assessment of effect.
 a) The primary endpoint is the size of the wound (to assess a reduction in size).
 b) Surrogate variables: Skin biopsies and blood samples, before and after treatment, in order to perform flow cytometry, to measure PCT and/or CRP and/or the differential white cell count in whole blood Eosinophil count.

Example 3

Treats Sent with a Composition of the Present Invention

Patients having comparable types of wounds will be divided into 3 treatment groups,
 the first being treated with a composition comprising an aqueous solution of:
 100 μg/g GM-CSF; 1% w/w HA (sodium hyaluronate); 10% w/w sucralfate;
 the second being treated with a composition that only comprises HA (1% w/w) and sucralfate (10% w/w);
 the third being treated with a composition that only comprises GM-CSF (100 μg/g) and sucralfate (10% w/w).

The compositions will be applied manually in an amount of 5 to 10 mL on the surface and subcutaneously along the edges and base of wounds. In each group of patients treated with different compositions, half of the treated patients are further treated with a roller tool with protrusions of 0.8 mm after topical application of the composition. The treatment will be given once a day during a period of 10 days and patients will be followed weekly for a minimum of six weeks.

It is expected that the treatment with the pharmaceutical composition comprising GM-CSF, sucralfate and hyaluronic acid will be more effective in inducing faster healing of the wounds than the other treatments.

By comparing the group of patients treated with compositions applied only manually and the group of patients treated with compositions applied by use of a roller tool, it is expected to be observed that the treatment with the roller tool is more effective.

Example 4

Treatment of a Venous Leg Ulcer in a Drug Addict

Patient: A person with a history of drug addiction. The patient will have suffered from a non-healing wound located at the right crural medial region for three years. The ulcer could have developed after an intravenous injection which produced a lesion that became infected and developed to an abscess.

The condition of the patient worsens and due to severe pain located to the wound, and severe exacerbations when moving around, the patient is referred to hospital. On examination, the patient presents with a circumferentially sloughing ulcer, which is bad smelling and with gross exudates.

The patient is admitted for debridement and treatment of right lower limb venous ulceration.

Vascular investigations include repeated arterial blood and peripheral toe pressure monitoring, which all are normal.

The patient is treated with different types of debridement and application of the first composition of Example 3 to the wound daily, combined with systemic antibiotics.

After some months, the wound will be expected to be almost be healed, significantly reduced in size and without exudates.

Example 5

Treatment of a Non-Healing Wound in a Diabetic Patient

The patient may be referred to the Outpatient Clinic by the Orthopedic Department for treatment of a non-healing wound on the ankle. The patient has been diagnosed with type 2 diabetes mellitus some years earlier. After an injury resulting in a fracture, the patient undergoes surgery.

The surgical wound develops into a non-healing wound accompanied by reduced mobility, constant pain and sleep deprivation, as a result of which the consumption of cigarettes and alcohol has increased and the diet is not being observed.

Blood tests are taken for evaluating diabetic control, inflammation and infection. There are no local signs of osteomyelitis, and the local surveillance cultures to identify wound infection or contamination are negative.

Treatment of the wound: The wound will be treated locally with debridement, application of the first composition of Example 3 to the area of the wound in combination with frequent change of the wound dressing, topical negative pressure treatment (TNPT) and prophylactic antibiotic administered by mouth.

After 6 months the wound begins to heal. There is contact with bone (1$^{st}$ metatarsal) at the bottom of the wound. The general medical condition of the patient is poor, which together with insufficient infection control results in spread of the infection. The end result is an abscess in the anteromedial plantar region.

The lack of infection control leads to extensive surgical wound revision with removal of the 1$^{st}$ and 2$^{nd}$ toes together with the 1$^{st}$ and 2$^{nd}$ metatarsal heads.

The next year, the patient is systematically monitored in the outpatient clinic with strict control of the diabetes and off-loading of the wound plus lifting the lower extremity to reduce the edema, while frequent debridement procedures are carried out.

The wound is healed by combined surgical and medical interventions with removal of all toes and metatarsal heads, topical negative pressure treatment (TNPT), daily application of the first composition of Example 3 formulated as a spray, frequent change of dressings, strict diabetic control and use of antibiotics. After 1.5 years the foot is almost healed.

REFERENCES

Brown C B, Pihl C E, Kaushansky K (1994) Mapping of human granulocyte-macrophage-colony-stimulating-factor domains interacting with the human granulocyte-macrophage-colony-stimulating-factor-receptor alpha-subunit. Eur J Biochem 225:873-880.

Burgess A W, Begley C G, Johnson G R, Lopez A F, Williamson D J, Mermod J J, Simpson R J, Schmitz A, DeLamarter J F (1987) Purification and properties of bacterially synthesized human granulocyte-macrophage colony stimulating factor. Blood 69:43-51.

Cebon J, Nicola N, Ward M, Gardner I, Dempsey P, Layton J, Duhrsen U, Burgess A W, Nice E, Morstyn G (1990) Granulocyte-macrophage colony stimulating factor from human lymphocytes. The effect of glycosylation on receptor binding and biological activity. J Biol Chem 265:4483-4491.

de Groot R P, Coffer P J, Koenderman L (1998) Regulation of proliferation, differentiation and survival by the IL-3/IL-5/GM-CSF receptor family. Cell Signal 10:619-628.

Diederichs K, Jacques S, Boone T, Karplus P A (1991) Low-resolution structure of recombinant human granulocyte-macrophage colony stimulating factor. J Mol Biol 221:55-60.

Gasson J C, Kaufman S E Weisbart R H, Tomonaga M, Golde D W (1986) High-affinity binding of granulocyte-macrophage colony-stimulating factor to normal and leukemic human myeloid cells. Proc Nati Acad Sci USA 83:669-673.

Gearing D P, King J A, Gough N M, Nicola N A (1989) Expression cloning of a receptor for human granulocyte-macrophage colony-stimulating factor. EMBO J 8:3667-3676.

Hayeshida K. Kitamura T, Gorman D M, Arai K, Yokota T, Miyajima A (1990) Molecular cloning of a second subunit of the receptor for human granulocyte-macrophage colony-stimulating factor (GM-CSF): reconstitution of a high-affinity GM-CSF receptor. Proc Natl Aced Sci USA 87:9655-9659.

Kaushansky K, O'Hara P J, Berkner K. Segal G M, Hagen F S, Adamson J W (1986) Genomic cloning, characterization, and multilineage growth-promoting activity of human granulocyte-macrophage colony-stimulating factor. Proc Natl Acad Sci USA 83:3101-3105.

Kitamura T, Hayashida K, Sakamaki K, Yokota T, Arai K, Miyajima A (1991) Reconstitution of functional receptors for human granulocyte/macrophage colony-stimulating factor (GM-CSF): evidence that the protein encoded by the AlC2B cDNA is a subunit of the murine GM-CSF receptor. Proc Natl Acad Sci USA 88:5082-5086.

Lopez A F, Vadas M A, Woodcock J M, Milton S E, Lewis A, Elliott M J, Gillis D, Ireland R, Olwell E, Park L S (1991) Interleukin-5, interleukin-3, and granulocyte-macrophage colony-stimulating factor cross-compete for binding to cell surface receptors on human eosinophils. J Biol Chem 266:24741-24747.

Makkonen T A, Minn H, Jekunen A, Vilja P, Tuominen J, Joensuu H (2000) Granulocyte macrophage-colony stimulating factor (GM-CSF) and sucralfate in prevention of radiation-induced mucositis: a prospective randomized study. Int J Radiat Oncol Biol Phys 46:525-534.

Martindale: The Complete Drug Reference, 34$^{th}$ edition ed. by Sweetman S C. ISBN: 0853695504/0-85369-550-4. Pharmaceutical Press, London, 2005.

Saarilahti K, Kajanti M, Joensuu T, Kouri M, Joensuu H (2002) Comparison of granulocyte-macrophage colony-stimulating factor and sucralfate mouthwashes in the prevention of radiation-induced mucositis: a double-blind prospective randomized phase III study. Int J Radiat Oncol Biol Phys 54:479-485.

Sato N, Sakamaki K, Terada N, Arai K, Miyajima A (1993) Signal transduction by the high-affinity GM-CSF receptor: two distinct cytoplasmic regions of the common beta subunit responsible for different signaling. EMBO J 12:4181-4189.

Shanafelt A B, Miyajima A, Kitamura T, Kastelein R A (1991a) The amino-terminal helix of GM-CSF and IL-5 governs high affinity binding to their receptors. EMBO J 10:4105-4112.

Shanafelt A B, Johnson K E, Kastelein R A (1991b) Identification of critical amino acid residues in human and mouse granulocyte-macrophage colony-stimulating factor and their involvement in species specificity. J Biol Chem 266:13804-13810.

Szoka F Jr, Papahadjopoulos D (1980) Comparative properties and methods of preparation of lipid vesicles (liposomes). Anne Rev Biophys Bioeng 9:467-508.

Wong G G, Witek J S, Temple P A, Wilkens K M, Leary A C, Luxenberg D P, Jones S S, Brown E L, Kay R M, Orr E C, et al. (1985) Human GM-CSF: molecular cloning of the complementary DNA and purification of the natural and recombinant proteins. Science 228:810-815.

Yeh B K, Eliseenkova A V, Plotnikov A N, Green D, Pinnell J, Polat T, Gritli-Linde A, Linhardt R J, Mohammad M (2002) Structural basis for activation of fibroblast growth factor signaling by sucrose octasulfate. Mol Cell Biol 22:7184-7192.

What is claimed is:

1. A method of alleviating a chronic wound in a subject comprising administering topically to the wound a composition formulated as a hydrogel, the composition comprising:
    a granulocyte-macrophage colony-stimulating factor (GM-CSF) having at least 95% sequence identity to SEQ ID. No. 2 at a concentration of 10 μg/g to 300 μg/g;
    sucralfate at a concentration of 5% w/w to 20% w/w; and
    a salt of hyaluronan at a concentration of 0.1% w/w to 10% w/w.

2. The method of claim 1, wherein the GM-CSF has a T115I substitution, wherein the substitution is positioned in accordance with the amino acid positions set forth in SEQ ID No. 1.

3. The method of claim 1, wherein the GM-CSF has a 1117T substitution, wherein the substitution is positioned in accordance with the amino acid positions set forth in SEQ ID No. 1.

4. The method of claim 1, wherein the chronic wound is a venous leg ulcer, venous foot ulcer, arterial leg ulcer, arterial foot ulcer, decubitus ulcer, pressure lesion, bedsore lesion, post-surgical ulcerous lesion, or a burn.

5. The method of claim 1, wherein said subject is a diabetic.

6. The method of claim 1, further comprising evaluating the healing process of said chronic wound.

7. The method of claim 1, further comprising administering a local anesthetic agent to said subject.

8. The method of claim 1, further comprising administering one or more antibacterial or antifungal agents to said subject.

9. The method of claim 1, wherein said composition comprises 50 μg/g of said GM-CSF.

10. The method of claim 1, wherein said composition comprises 80 μg/g to 120 μg/g of said GM-CSF.

11. The method of claim 1, wherein said composition comprises 8-15% w/w of sucralfate.

12. The method of claim 1, wherein said composition comprises 20% w/w of sucralfate.

13. The method of claim 1, wherein said composition comprises 0.2-1.2% w/w of the salt of hyaluronan.

14. The method of claim 1, wherein said composition comprises 0.2% w/w of the salt of hyaluronan.

15. The method of claim 1, wherein said composition is formulated as a paste.

16. The method of claim 1, wherein said composition provides moisture to the chronic wound.

17. The method of claim 16, wherein the moisture facilitates alleviation to said chronic wound.

18. The method of claim 1, wherein the chronic wound is a venous leg ulcer, venous foot ulcer, diabetic leg ulcer, diabetic foot ulcer, arterial leg ulcer, arterial foot ulcer, decubitus ulcer, pressure lesion, bedsore lesion, post-surgical ulcerous lesion, or a burn.

19. The method of claim 1, wherein the salt of hyaluronan comprises a sodium salt, a potassium salt, a magnesium salt, a calcium salt, or a combination thereof.

20. The method of claim 1, wherein the salt of hyaluronan comprises a sodium salt.

21. The method of claim 1, wherein said GM-CSF is formulated in a liposome.

\* \* \* \* \*

UNITED STATES PATENT AND TRADEMARK OFFICE
CERTIFICATE OF CORRECTION

Page 1 of 3

PATENT NO. : 11,813,309 B2
APPLICATION NO. : 16/366898
DATED : November 14, 2023
INVENTOR(S) : Lars Heslet It is certified that error appears in the above-identified patent and that said Letters Patent is hereby corrected as shown below:

On the Title Page

Column 1 (Item (72) Inventor), Line 1, after "Heslet," insert -- (Deceased); --.

In the Specification

Column 1, Line 25, delete "26Sequence" and insert -- 26_Sequence --.

Column 1, Line 60-61, delete "ischemic," and insert -- ischemia, --.

Column 5, Line 35, delete "1991 b;" and insert -- 1991b; --.

Column 5, Line 38, delete "ID," and insert -- D, --.

Column 6, Line 9, delete "al, (1966)" and insert -- al. (1986) --.

Column 7, Line 18, delete "Ala" and insert -- Ala, --.

Column 7, Line 18, delete "Lou," and insert -- Leu, --.

Column 7, Line 26, delete "monoamine" and insert -- monoamino --.

Column 7, Line 27, delete "monoarnidocarboxylic" and insert -- monoamidocarboxylic --.

Column 7, Line 28, delete "Asn." and insert -- Asn, --.

Column 8, Line 17, delete "collagen)," and insert -- collagen). --.

Column 8, Line 18, delete "(h)" and insert -- (b) --.

Signed and Sealed this
Ninth Day of April, 2024

Katherine Kelly Vidal
*Director of the United States Patent and Trademark Office*

CERTIFICATE OF CORRECTION (continued)
U.S. Pat. No. 11,813,309 B2

Column 9, Line 67, delete "T1151" and insert -- T115I --.

Column 10, Line 34 (approx.), delete "ASHYKOHCPP" and insert -- ASHYKQHCPP --.

Column 10, Line 35 (approx.), delete "CWEPVQE" and insert -- CWEPVQE. --.

Column 11, Line 42, delete "sucralfate" and insert -- sucralfate. --.

Column 11, Line 53-54, delete "glucopyranosylsultate" and insert -- glucopyranosylsulfate --.

Column 15, Line 44, delete "patients" and insert -- patient's --.

Column 16, Line 31, delete "Preemptive treatment and/or allevation" and insert -- Pre-emptive treatment and/or alleviation --.

Column 18, Line 11, delete "I-serine]" and insert -- l-serine] --.

Column 18, Line 12, delete "I-serine)" and insert -- l-serine] --.

Column 18, Line 13, delete "I-serine]" and insert -- l-serine] --.

Column 18, Line 29, delete "AL" and insert -- AL. --.

Column 19, Line 5, delete "8:" and insert -- 8; --.

Column 23, Line 47, delete "granulocyte-macrophage-colony stimulating factor" and insert -- granulocyte-macrophage-colony-stimulating factor --.

Column 23, Line 64, after "embodiments" insert -- 1 to 3 --.

Column 24, Line 62, delete "ED" and insert -- ID --.

Column 25, Line 14, delete "occouring" and insert -- occurring --.

Column 25, Line 22, delete "occouring" and insert -- occurring --.

Column 25, Line 38, delete "e" and insert -- the --.

Column 26, Line 14 (approx.), delete "why" and insert -- w/w --.

Column 27, Line 49, delete "blood" and insert -- blood. --.

Column 27, Line 54, delete "Treats Sent" and insert -- Treatment --.

Column 28, Line 46, delete "almost be" and insert -- almost --.

CERTIFICATE OF CORRECTION (continued)
U.S. Pat. No. 11,813,309 B2

Column 29, Line 59, delete "Nati" and insert -- Natl --.

Column 29, Line 65, delete "Hayeshida K." and insert -- Hayashida K, --.

Column 30, Line 2, delete "Aced" and insert -- Acad --.

Column 30, Line 4, delete "K." and insert -- K, --.

Column 30, Line 14, delete "AlC2B" and insert -- AIC2B --.

Column 30, Line 57 (approx.), delete "Anne" and insert -- Annu --.

Column 30, Line 64, delete "Mohammad" and insert -- Mohammadi --.

In the Claims

Column 33, Line 8 (approx.), Claim 1, delete "ID." and insert -- ID --.

Column 33, Line 13 (approx.), Claim 2, delete "T1151" and insert -- T115I --.

Column 33, Line 17 (approx.), Claim 3, delete "1117T" and insert -- I117T --.

SEQUENCE LISTING

<160> NUMBER OF SEQ ID NOS: 2

<210> SEQ ID NO 1
<211> LENGTH: 144
<212> TYPE: PRT
<213> ORGANISM: Homo Sapiens

<400> SEQUENCE: 1

| Met | Trp | Leu | Gln | Ser | Leu | Leu | Leu | Gly | Thr | Val | Ala | Cys | Ser | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ser | Ala | Pro | Ala | Arg | Ser | Pro | Ser | Pro | Ser | Thr | Gln | Pro | Trp | Glu | His |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Asn | Ala | Ile | Gln | Glu | Ala | Arg | Arg | Leu | Leu | Asn | Leu | Ser | Arg | Asp |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Thr | Ala | Ala | Glu | Met | Asn | Glu | Thr | Val | Glu | Val | Ile | Ser | Glu | Met | Phe |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Asp | Leu | Gln | Glu | Pro | Thr | Cys | Leu | Gln | Thr | Arg | Leu | Glu | Leu | Tyr | Lys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gln | Gly | Leu | Arg | Gly | Ser | Leu | Thr | Lys | Leu | Lys | Gly | Pro | Leu | Thr | Met |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Met | Ala | Ser | His | Tyr | Lys | Gln | His | Cys | Pro | Pro | Thr | Pro | Glu | Thr | Ser |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| Cys | Ala | Thr | Gln | Ile | Ile | Thr | Phe | Glu | Ser | Phe | Lys | Glu | Asn | Leu | Lys |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Asp | Phe | Leu | Leu | Val | Ile | Pro | Phe | Asp | Cys | Trp | Glu | Pro | Val | Gln | Glu |
|-----|-----|-----|-----|-----|-----|-----|-----|-----|-----|-----|-----|-----|-----|-----|-----|
|     |     |     | 130 |     |     |     |     | 135 |     |     |     |     | 140 |     |     |

<210> SEQ ID NO 2
<211> LENGTH: 127
<212> TYPE: PRT
<213> ORGANISM: Homo Sapiens

<400> SEQUENCE: 2

| Ala | Pro | Ala | Arg | Ser | Pro | Ser | Pro | Ser | Thr | Gln | Pro | Trp | Glu | His |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Val | Asn | Ala | Ile | Gln | Glu | Ala | Arg | Arg | Leu | Leu | Asn | Leu | Ser | Arg | Asp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Ala | Ala | Glu | Met | Asn | Glu | Thr | Val | Glu | Val | Ile | Ser | Glu | Met | Phe |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Asp | Leu | Gln | Glu | Pro | Thr | Cys | Leu | Gln | Thr | Arg | Leu | Glu | Leu | Tyr | Lys |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Gln | Gly | Leu | Arg | Gly | Ser | Leu | Thr | Lys | Leu | Lys | Gly | Pro | Leu | Thr | Met |
|-----|-----|-----|-----|-----|-----|-----|-----|-----|-----|-----|-----|-----|-----|-----|-----|
|     |     |     |     | 65  |     |     |     |     | 70  |     |     |     |     | 75  |     |

| Met | Ala | Ser | His | Tyr | Lys | Gln | His | Cys | Pro | Pro | Thr | Pro | Glu | Thr | Ser |
|-----|-----|-----|-----|-----|-----|-----|-----|-----|-----|-----|-----|-----|-----|-----|-----|
| 80  |     |     |     |     | 85  |     |     |     |     | 90  |     |     |     |     | 95  |

| Cys | Ala | Thr | Gln | Ile | Ile | Thr | Phe | Glu | Ser | Phe | Lys | Glu | Asn | Leu | Lys |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Asp | Phe | Leu | Leu | Val | Ile | Pro | Phe | Asp | Cys | Trp | Glu | Pro | Val | Gln | Glu |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |